United States Patent [19]

Pollet et al.

[11] 4,292,402
[45] Sep. 29, 1981

[54] LIGHT-SENSITIVE SILVER HALIDE MATERIALS CONTAINING FLUORINE-CONTAINING SURFACTANTS

[75] Inventors: Robert J. Pollet, Vremde; Hendrik E. Kokelenberg, Merksem; Rafaël P. Samijn, Wilrijk; Francis J. Sels, Kontich; Frans J. Villé, Edegem; Nikolaas C. de Jaeger, Mortsel, all of Belgium

[73] Assignee: Agfa-Gevaert, N.V., Mortsel, Belgium

[21] Appl. No.: 120,111

[22] Filed: Feb. 8, 1980

[30] Foreign Application Priority Data

Feb. 28, 1979 [GB] United Kingdom ............... 07040/79

[51] Int. Cl.$^3$ .......................... G03C 1/76; G03C 1/38
[52] U.S. Cl. ................................... 430/631; 430/536; 430/537; 430/637; 430/950; 430/961
[58] Field of Search ............... 430/536, 523, 546, 631, 430/637, 950, 961, 537

[56] References Cited

U.S. PATENT DOCUMENTS

| | | | |
|---|---|---|---|
| 3,837,863 | 9/1974 | Sakazume et al. | 430/631 |
| 3,850,642 | 11/1974 | Bailey et al. | 430/631 |
| 4,047,804 | 9/1977 | Stephens | 430/950 |
| 4,201,586 | 5/1980 | Hori et al. | 430/631 |

Primary Examiner—J. Travis Brown

Attorney, Agent, or Firm—A. W. Breiner

[57] ABSTRACT

Fluorine-containing surfactants according to formula $(Rf-X)_n-A-L-Z$ wherein $Rf$ is a short-chain fluorine-containing group derived from hexafluoropropylene or trifluorochloroethylene, X is —O—, —S—, or —SO$_2$—, n is at least 2, the Rf groups being same or different, L is a monovalent bond or a bivalent bridging group such as —COO—alkylene, —CONR$^1$—alkylene, or —SO$_2$NR$^1$—alkylene, wherein R$^1$ is hydrogen or C$_1$–C$_5$ alkyl, and Z represents a hydrophilic polyoxyethylene group or a hydrophilic group such as

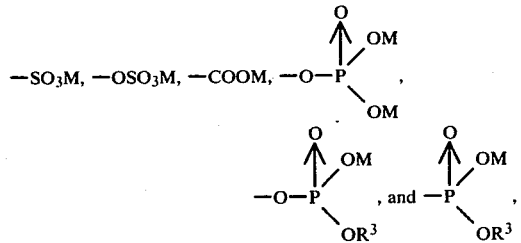

wherein M is hydrogen, an alkali metal, ammonium, or organic ammonium, and R$^3$ is alkyl; A is an aliphatic, aromatic, or aliphatic-aromatic group. These surfactants can be used in hydrophilic colloid layers, which may form part of light-sensitive silver halide materials.

7 Claims, No Drawings

LIGHT-SENSITIVE SILVER HALIDE MATERIALS CONTAINING FLUORINE-CONTAINING SURFACTANTS

The present invention relates to novel fluorine-containing surface-active agents, to coating compositions comprising a hydrophilic colloid binder and such fluorine-containing surface-active agent, and more particularly to light-sensitive silver halide materials comprising one or more hydrophilic colloid layers, especially gelatin layers at least one of which comprises such fluorine-containing surface-active agent.

The coating of film-forming compositions comprising hydrophilic colloid(s) to a support, more particularly the coating of silver halide layer(s), intermediate layer(s), antistress layer(s), filter layer(s), antihalation layer(s), matting layer(s) etc. for the formation of photographic materials should be performed uniformly and at economic production speeds.

A coating composition containing a hydrophilic colloid binder should be fully hydrophilic so that a uniform layer can be formed therewith. A uniform layer comprises no hydrophobic inclusions, since any such inclusions would give rise to repellency areas and/or spots as a result of differentiated surface-active behaviour. Repellency areas and/or spots are commonly referred to as dry coating areas, streaks and/or so-called comets.

If the layer containing a hydrophilic colloid is an outer or surface layer of a light-sensitive silver halide emulsion material to be processed by a hydrophilic processing composition, its entire surface should be hydrophilic so as to permit uniform and simultaneous reaction with, or penetration by the processing composition. If the layer containing a hydrophilic colloid is to be coated with (an)other layer(s) e.g. in the production of a multilayer silver halide material, its entire surface should be hydrophilic so as to permit uniform rewetting by a hydrophilic coating composition to form said other layer(s).

As to outer layers of silver halide emulsion materials it is not only of importance that their entire surface be hydrophilic so as to be re-wettable during processing, but also that they are capable of drying uniformly. Outer layers showing areas of different hydrophobicity or hydrophilicity also have different retouchability as well as differences in density reading upon drying, even though the silver coverage is uniform all over the surface of the light-sensitive material.

In the case a layer comprising a hydrophilic colloid is to be overcoated with another hydrophilic layer, the maximum speed of the moving layer to be overcoated, at which no repellency occurs, can be increased to the extent the surface to be overcoated has a more hydrophilic character.

A large variety of surfactants have been proposed for use in hydrophilic colloid coating compositions to fulfil the hydrophilicity requirements thereof. Surface-active agents are also employed to disperse in these coating compositions such hydrophobic ingredients as dyes, colour couplers, competing couplers, stabilizers, matting agents etc. and to reduce the adverse effect of these compounds on the hydrophilicity of the layers concerned. Whereas a given surfactant may have a favourable effect in one respect, it may be ineffective or even disadvantageous in another respect, for which other surfactants may then be particularly effective. Therefore, hydrophilic colloid coating compositions often comprise more than one surfactant. Moreover, not all compounds known to reduce the surface-tension outside the field of photography e.g. for use in detergents, are suitable for use in hydrophilic colloid layers of photographic materials, especially in light-sensitive silver halide materials, either because they impair the photographic characteristics or because they do not have the desired surface activity in these hydrophilic colloid coating compositions.

Among the surfactants that have been proposed lately for use in light-sensitive silver halide materials there is the class of fluorine-containing surfactants having a terminal hydrophobic long-chain perfluorocarbon group and a terminal hydrophilic non-ionic, anionic, cationic, or amphoteric group. In this connection there can be referred to the published German Patent Applications Nos. 1,950,121 filed Oct. 4, 1969 by du Pont de Nemours and 1,942,665 filed Aug. 21, 1969 by Ciba A. G., and to the Belgian patent specifications Nos. 742,680 filed Dec. 5, 1969 and 766,835 filed May 7, 1971, both by Gevaert-Agfa N. V.

Most of the fluorinated surface-active agents are expensive, commercially available products or they can be derived from expensive, commercially available, fluorine-containing compounds. The use of such expensive surfactants in silver halide emulsion materials has a bearing, of course, on the production costs thereof. On the other hand these compounds are highly desirable for use in light-sensitive silver halide materials, since they confer to these materials very specific characteristics such as e.g. a uniform coating, enhanced production speed, elimination of dry-coating areas, improved antistatic behaviour, etc.

It is an object of the present invention to provide novel fluorine-containing surface-active agents.

Another object of the present invention is to provide fluorine-containing surface-active agents that are cheaper as compared with known fluorine-containing surface-active agents.

A further object of the present invention is to provide coating compositions comprising a hydrophilic colloid binder and at least one novel fluorine-containing surface-active agent.

A further object of the present invention is to provide light-sensitive silver halide materials containing at least one hydrophilic colloid layer comprising at least one novel fluorine-containing surface-active agent.

Other objects of the invention will become apparent from the disclosure hereinafter.

The above objects are accomplished with the aid of surface-active agents, which in addition to (a) hydrophilic group(s) contain at least two hydrophobic short-chain fluorine-containing groups derived from the inexpensive commercially available trifluorochloroethylene or hexafluoropropylene.

The present invention more particularly provides fluorine-containing surface-active agents corresponding to the following general formula:

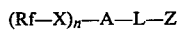

wherein
Rf represents a short-chain fluorine-containing group derived from hexafluoropropylene or trifluorochloroethylene, such short-chain group corresponding to one of the formulae Y—HCF—CF$_2$—, Y—CF=CF—, and F$_2$C=CF—CF$_2$—wherein Y represents chlorine or trifluoromethyl, X represents oxygen, sulphur, or sulphonyl, n represents an integer of at least 2, the Rf groups being same or different, L represents a monovalent bond or a bivalent group selected from —COO—alkylene—, —CONR$^1$—alkylene—, and —SO$_2$NR$^1$—alkylene—, wherein R$^1$ is hydrogen or C$_1$–C$_5$ alkyl, and Z represents (1) a hydrophilic polyoxyethylene group, e.g. —O(CH$_2$CH$_2$O)$_m$R$^2$ wherein m is a positive integer, preferably from 4 to 40 and R$^2$ is hydrogen, or C$_1$–C$_5$ alkyl, which may be substituted e.g. by carboxy, sulpho or sulphato in acid or salt form, or (2) a hydrophilic group selected from the group consisting of —SO$_3$M, —OSO$_3$M, —COOM,

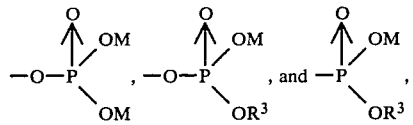

wherein M is hydrogen, an alkali metal, ammonium, or organic ammonium, and R$^3$ is alkyl, A represents a straight-chain or branched-chain aliphatic hydrocarbon group e.g. C$_1$–C$_{20}$ alkylene, an aromatic hydrocarbon group e.g. phenylene and naphthalene or a mixed aliphatic-aromatic hydrocarbon group, which groups may be substituted or not; A being an aromatic hydrocarbon group when L is a monovalent bond and Z is a hydrophilic polyoxyethylene group.

The surface-active agents of the above formula are prepared by addition reaction between hexafluoropropylene or trifluorochloroethylene and hydroxy- or mercapto-substituted aliphatic or aromatic compounds containing (a) said hydrophilic group(s), or hydroxy- or mercapto-substituted aliphatic or aromatic compounds, in which (a) said hydrophilic group(s) is (are) introduced subsequently.

A very interesting class of fluorine-containing surface-active compounds according to the present invention are those that can be prepared in a very convenient and reproducible way by addition reaction between hexafluoropropylene or trifluorochloroethylene and a di- or trihydroxy-substituted benzoic acid, subsequent alkaline hydrolysis, and optionally further conversion of the carboxy group. These aromatic compounds correspond to the above general formula wherein A is phenylene, n is 2 or 3 and L—Z together are —COR wherein R is (a) OM wherein M is hydrogen, alkali metal, ammonium, organic ammonium, or (CH$_2$CH$_2$O)$_p$R$^4$ wherein R$^4$ is hydrogen or C$_1$–C$_5$ alkyl, which may be substituted by carboxy, sulpho or sulphato in acid or salt form, and p is a positive integer, preferably from 4 to 40, or (b)

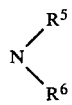

wherein R$^5$ is hydrogen or C$_1$–C$_5$ alkyl or has the same significance as R$^6$, R$^6$ is C$_1$–C$_{10}$ alkyl substituted by carboxy or sulpho in acid or salt form, or (CH$_2$CH$_2$O)$_z$R$^7$, wherein R$^7$ is hydrogen or C$_1$–C$_5$ alkyl, which may be substituted by carboxy, sulpho, or sulphato in acid or salt form, and z is a positive integer, preferably from 4 to 40.

The number of fluorine-containing groups in the above formulae is preferably 2 or 3.

Representative examples of fluorine-containing surface-active agents corresponding to the above general formula and prepared as described hereinafter are given in the following table 1.

In the structural formulae of the compounds listed, the structures given for the fluorine-containing groups (Rf) are the apparent structures established by gas chromatographic analysis techniques. According to high pressure liquid chromatography it was found however, that a given Rf-group can have one of the structures given hereinbefore and even that mixtures of compounds with such different structures for the Rf-group are obtained. This means that in a compound the Rf-groups may be same or different.

Nevertheless it was found that these differences in the Rf structures of any compound or mixture of compounds according to the invention do not influence the characteristics of such compound or mixture as a surface-active agent or as an antistat. Consequently, it is not necessary to separate the different fractions. Yet, they could be separated and used individually, if desired.

TABLE 1

Compound 1

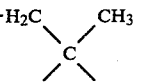

Compound 2

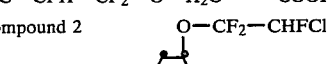

Compound 3

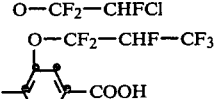

Compound 4

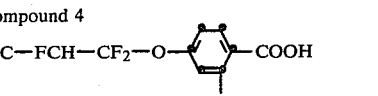

Compound 5

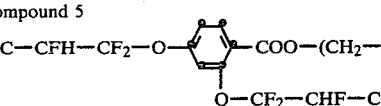

Compound 6

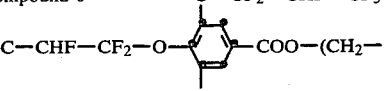

Compound 7

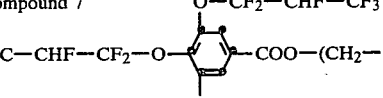

Compound 8

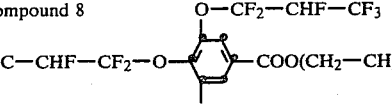

TABLE 1-continued

Compound 9

F$_3$C—CHF—CF$_2$—O—[benzene with O—CF$_2$—CHF—CF$_3$ (top) and O—CF$_2$—CHF—CF$_3$ (bottom)]—COO(CH$_2$—CH$_2$—O)$_n$—CH$_3$ n = 16 to 17

Compound 10

F$_3$C—CHF—CF$_2$—O—[benzene with O—CF$_2$—CHF—CF$_3$ (top) and O—CF$_2$—CHF—CF$_3$ (bottom)]—CONH—CH$_2$—CH$_2$—SO$_3$Na Compound 11

ClFHC—CF$_2$—O—[benzene with O—CF$_2$—CHFCl (top) and O—CF$_2$—CHFCl (bottom)]—CONH—CH$_2$—CH$_2$—SO$_3$Na Compound 12

F$_3$C—CHF—CF$_2$—O—[benzene with O—CF$_2$—CHF—CF$_3$ (top) and O—CF$_2$—CHF—CF$_3$ (bottom)]—CONH(CH$_2$—CH$_2$—O)$_{17}$H Compound 13

ClHFC—CF$_2$—O—[benzene with O—CF$_2$—CHF—CF$_3$ (top) and O—CF$_2$—CHFCl (bottom)]—CONH—(CH$_2$)$_{10}$—COONa Compound 14

F$_3$C—CFH—CF$_2$—O—[benzene with O—CF$_2$—CFH—CF$_3$ (bottom)]—SO$_3$Na

Compound 15

F$_3$C—CFH—CF$_2$—O—[benzene with OCF$_2$—CFH—CF$_3$ (top) and OCF$_2$—CFH—CF$_3$ (bottom)]—SO$_3$H Compound 16

F$_3$C—CFH—CF$_2$—O—[benzene with O—CF$_2$—CFH—CF$_3$ (top) and O—CF$_2$—CFH—CF$_3$ (bottom)]—SO$_3$H · N(CH$_2$CH$_2$OH)$_3$ The above compounds are prepared as described in the preparations hereinafter.

PREPARATION 1: COMPOUND 1

1 Mole of 2,2-bis(hydroxymethyl)propionic acid methyl ester together with 0.3 mole of potassium hydroxide, 1 liter of dimethylformamide, and 3.75 moles of hexafluoropropylene are heated at 80° C. for 6 hours in an autoclave. The oil obtained is washed with water and dissolved in 3 liters of methanol and 0.5 liter of 5 N sodium hydroxide.

The solution is refluxed for 3 hours, then poured into 7 liters of water, and acidified with 5 N hydrochloric acid. The free acid settles in the form of an oil. Yield: 60–65%.

PREPARATION 2: COMPOUND 2

1 Mole of 2,4,6-trihydroxybenzoic acid ethyl ester together with 0.15 mole of potassium hydroxide, 0.3 liter of acetone, and 3.75 moles of trifluorochloroethylene are heated at 90°–100° C. for 3 hours in an autoclave. The product boiling at 154°–158° C./1.5 mm Hg is washed with water and hydrolysed to the free acid. Yield: 40%. Melting point: 76° C.

PREPARATION 3: COMPOUND 3

1 mole of gallic acid is dissolved in 1.5 liters of dimethylformamide (or ethanol) and 0.6 liter of triethylamine. 3.75 moles of hexafluoropropylene are conducted through the solution at 20° to 25° C. at atmospheric pressure. After the addition of 8 liters of water and acidification with 5 N hydrochloric acid the product settles in the form of an oil. Yield: 60%.

PREPARATION 4: COMPOUND 4

Compound 4 is prepared by addition reaction of hexafluoropropylene with 2,4-dihydroxybenzoic acid methyl ester as described for compound 2. The fraction boiling at 124°–130° C./3 mm Hg is saponified to the free acid (oil). Yield: 30%.

PREPARATION 5: COMPOUND 5

Compound 4 is refluxed with thionyl chloride to convert it into the corresponding acid chloride boiling at 114°–117° C./2 mm Hg. Yield: 58%. 1 mole of the acid chloride is stirred with 1 mole of methoxypolyglycol having a molecular weight of 750 and 1 mole of triethylamine in 3 liters of toluene for 48 hours. The triethylamine hydrochloride is filtered off and the filtrate is concentrated by evaporation. A very viscous oil is obtained. Yield: 100%.

Preparations 6, 7, 8, 9, and 12 are carried out analogously to that of compound 5 by converting compound 3 into the corresponding acid chloride boiling at 118°–123° C./0.7 mm Hg. (Yield: 55%). The acid chloride is then made to react with polyglycol 400, polyglycol 200, polyglycol 600, methoxypolyglycol 750, and aminopolyglycol (n=approximatively 17) respectively to form the corresponding compounds 6, 7, 8, 9, and 12.

PREPARATION 10: COMPOUND 10

1 Mole of triethylamine and 1 mole of the sodium salt of taurine are dissolved in 4 liters of methanol. 1 mole of the acid chloride of compound 5, dissolved in 4 liters of methylene chloride is added thereto. The mixture is stirred for 24 hours. Subsequently, the solvent is evaporated. The residue is dissolved in acetone, filtered off and the filtrate is concentrated by evaporation. Melting point: approximatively 120° C.

Yield: 75%.

PREPARATION 11: COMPOUND 11

3,4,5-tri(2H,-2-chloro-trifluoroethoxy)benzoic acid is prepared analogously to compound 2, but starting from gallic acid. This is converted analogously to the synthesis of compound 10 into the final product. Melting point: approximatively 230° C. Yield: 88%.

PREPARATION 13: COMPOUND 13

By addition of trifluorochloroethylene to 2,4-dihydroxybenzoic acid ethyl ester (analogously to compound 2; yield: 48%; boiling point: 125° C./0.9 mm Hg), saponification to the free acid (yield: 93%; melting point: 67° C.) and conversion with thionyl chloride, the acid chloride (yield: 90%; boiling point: 122° C./0.6 mm Hg) is obtained. 1 mole of the acid chloride is added dropwise to a solution of 1 mole of ω-amino-undecanoic acid sodium salt and 1 mole of triethylamine in 2 liters of methanol. After the reaction 1 mole of sodium hydroxide is added, the sodium chloride formed is filtered off, and the solution is concentrated by evaporation. Yield: 86%.

Melting point: approximatively 230° C.

Preparation 14: COMPOUND 14

Compound 14 is obtained analogously to compound 3 by addition of hexafluoropropylene to the potassium salt of hydroquinone sulphonic acid. The resulting compound is an oil. Yield: 94%.

PREPARATION 15: COMPOUND 15

1 Mole of pyrogallol was dissolved in 1 liter of ethanol and 0.5 liter of triethylamine, 3 moles of hexafluoropropylene are conducted through the solution at room temperature. Subsequently, the mixture is poured out in water. The separating oil is extracted with ether, dried over sodium sulphate; the ether is evaporated and the resulting oil distilled. Yield: 75%. Boiling range at 0.5 mm Hg: 87°–89° C. The distillate is added to 2.5 liters of oleum (20% $SO_3$). The mixture is stirred for 4 hours at room temperature and then poured out on ice. The aqueous layer is extracted with ether. The ethereal solution is dried over sodium sulphate; the ether is distilled off and the resulting residue is washed with hexane to give a waxy solid. Yield: 50%.

PREPARATION 16: COMPOUND 16

1 mole of phloroglucinol is dissolved in 1200 ml of ethanol and 600 ml of triethylamine. Hexafluoropropylene is introduced into the solution until there is no absorption anymore. The solution is concentrated by evaporation. The resulting oil is extracted with methylene chloride. The methylene chloride layer is washed with water and concentrated by evaporation. The oil is distilled. Yield: 390 g. Melting point: 92°–96° C./1.2 mm Hg.

25 ml of oleum (65% $SO_3$) are added dropwise to 0.1 mole of the above-mentioned oil at approximately 40° C. The mixture is stirred for 3 h. Next, 250 ml of dichloroethane are added thereto. The sulphuric acid is separated from the dichloroethane layer and 5.5 ml of water are added to the dichloroethane. The sulphuric acid formed is separated off again. 20 ml of triethanolamine are added to the dichloroethane layer. Compound 16 settles as an oil from the solution. The oil is washed twice with dichloroethane and then extracted with 250 ml of acetone. The acetone layer is filtered with a filter aid and concentrated by evaporation.

Yield: 31 g of resinous product.

The fluorine-containing compounds according to the present invention provide a high surface-activity comparable to that of the known fluorinated surfactants with long-chain fluorine-containing hydrophobic groups. The compounds of the invention offer the advantage of being far less expensive.

Hydrophilic colloid coating compositions containing surfactants according to this invention can be applied to dry surfaces as well as to wet surfaces and yield uniform layers with reduced formation of repellency spots, which layers can be overcoated easily in wet as well as in dry conditions.

The hydrophilic colloid layers containing the surfactants according to the invention may be either light-sensitive layers or not. Light-sensitive and other hydrophilic colloid layers of photographic materials containing surface-active compounds according to the present invention show improved wettability by photographic processing liquids.

Surface-active agents of the invention containing a polyoxyethylene group having not more than 25 recurring ethylene oxide units also provide hydrophilic colloid layers with favourable antistatic properties.

Consequently, the compounds of the present invention are used primarily for their surface-active properties but they can also be applied in coating compositions to reduce the electrostatical charge in the layers obtained. Moreover, they can be used as a valuable aid in the dispersing of hydrophobic particles, e.g. matting agents such as Teflon (registered trade mark of du Pont for polytetrafluoroethylene) in hydrophilic colloid binder compositions for forming layers of e.g. photographic materials.

The short-chain fluorinated surfactants of the present invention can thus be present in hydrophilic colloid compositions for a variety of purposes.

The present invention provides in particular coating compositions, which comprise a hydrophilic colloid and at least one surfactant as defined above for forming hydrophilic colloid layers of photographic materials e.g. photographic silver halide materials.

The invention further provides materials comprising a support and one or more hydrophilic colloid layers, especially photographic silver halide materials comprising a support and at least one silver halide emulsion layer, the said materials comprising at least one hydrophilic colloid layer containing at least one surfactant as defined above.

It has been found that surfactants according to the present invention improve the coating characteristics of coating compositions already at a concentration as low as 0.01% by weight in respect of the weight of solids. Larger concentrations, however, can also be used but in general the concentration does not exceed 5% by weight based on the weight of solids. In coating compositions intended for being coated as hydrophilic colloid layers in photographic silver halide materials said surfactants are usually present in amounts from 0.02 to 2% based on the weight of dry colloid e.g. gelatin.

The surfactants according to the invention are particularly suitable for use in a coating composition comprising gelatin as hydrophilic colloid, either as an aqueous solution of gelatin or as a photographic emulsion, which ordinarily is composed of an aqueous solution of gelatin containing as the light-sensitive material therein, a silver halide such as silver bromide, silver chloride, silver iodide, or mixtures thereof or another light-sensitive substance. The emulsion may contain other added substances such as sensitizing dyes, hardeners, stabilizers, pH-adjusting compounds, colour couplers, antifogging agents, development accelerators, thickening agents, developing agents, softening agents, or the like. For instance, the surfactants of the invention are useful in gelatin photographic emulsions, not only those which are non-optically sensitized e.g. X-ray emulsions, but also in orthochromatic and panchromatic emulsions as used e.g. in colour materials. This also includes gelatin emulsions intended for colour photography such as those containing colour forming couplers and fine-grain emulsions of the Lippmann type.

The surfactants according to the present invention are also very useful in various other types of coating compositions in which gelatin or other hydrophilic colloids are important constituents, e.g. in hydrophilic colloid coating compositions to be applied as antihalation layer to the rear or front side of the support of a photographic material, or to be applied as antistress layer, filter layer, intermediate layer, anticurling layer etc., which layers may contain any other ingredients such as filling agents, matting agents, hardening agents, antistatic agents, antifriction agents, or in any type of hydrophilic colloid layer, which is coated from a composition comprising an aqueous solution of hydrophilic colloid e.g. an image-receiving layer as used in the silver complex diffusion transfer reversal process or in colour diffusion transfer processes.

The surfactants of the present invention have also favourable properties for dispersing or emulsifying substances in hydrophilic colloid compositions, which as a result of the presence of said coating aids also show improved coating characteristics. For instance they are suitable as dispersing agent or emulsifying agent for substances that are to be incorporated into layers comprising a hydrophilic colloid and that would give rise to the formation of repellency spots in said layers when no compounds according to the invention were present. They are particularly suitable for dispersing matting agents, in particular polytetrafluoroethylene, in hydrophilic colloid composition for forming a surface coating of a photographic silver halide material e.g. X-ray material. In layers containing matting agents one or more known surface-active agents can be used as dispersing agent e.g. ethoxylated nonylphenol, perfluorocaprylic acid ammonium salt, ethoxylated perfluorocaprylamide and/or alkane sulphonates e.g. sodium tetradecylsulphonate whereas one or more fluorine-containing surfactants according to the present invention e.g. compounds 5, 6, 7, 9, and 10 of the table hereinbefore can be employed as coating aid or vice versa.

Sometimes it may be advisable to employ more than one surface-active compound according to the present invention to reach optimum results due to the various characteristics these compounds confer to hydrophilic colloid coating compositions as well as to dried layers formed thereof. For instance, one compound may be preferred because it does not increase the foam level, others because they better reduce the electrostatical charge, and still others because they excel in remedying the dry coating defects etc. Blends of surface-active compounds can often provide characteristics superior to those provided by each of the surface-active compounds alone. For the same purpose it is also possible to use blends of surface-active compounds according to the invention with surfactants known in the art e.g. dialkylsulphosuccinic acid salts such as sodium diisooctylsulphosuccinate, salts of alkyl sulphuric acids, salts of alkylsulphonic acids, salts of alkylaryl polyether sulphuric acids and salts of alkylaryl polyether sulphonic acids, carboxyalkylated polyethylene glycolethers or esters such as iso—$C_8H_{17}$—$C_6H_4$(O—$CH_2$—$CH_2$-)$_8$—$OCH_2COONa$ known from U.S. Pat. No. 3,663,229 of Frans Jan Ville, Jozef Frans Willems and Hendrik Adolf Pattijn, issued May 16, 1972, and other fluorinated surfactants e.g. of the type described in the published German Patent Applications Nos. 1,950,121 and 1,942,665 and the Belgian patent specification No. 742,680, all mentioned hereinbefore. Hydrophilic colloid layers containing the surfactants of the present invention can contain other perfluorinated compounds for improving the physical properties e.g. the fluorinated compounds described in French patent specification No. 2,272,416 filed Dec. 30, 1974 by Fuji Photo Film Company Limited and the N-(perfluoroalkylsulphonyl)carbamic acid esters of polyalkylene oxides described in German Patent Application DE-OS No. 2,238,740 filed Aug. 5, 1972 by Bayer A. G., for reducing the sticking tendency of photographic surface layers against other surfaces e.g. of X-ray materials against cassette walls.

In this connection it should be mentioned that some known anionic surfactants such as straight-chain and branched-chain aliphatic sulphates, sulphonates and carboxylates, though they may have favourable properties for use as coating aids in hydrophilic colloid coating compositions, are often unsatisfactory in that they have a disadvantageous effect on the antistatic properties of the layers coated from these compositions and that it was found possible to reduce or eliminate this disadvantageous effect by using instead of these known coating aids or in addition thereto fluorinated surface-active compounds as defined above.

Although the surfactants according to the present invention are mainly intended for use in coating compositions comprising gelatin as hydrophilic colloid, they can also be used as surfactants for coating compositions comprising other hydrophilic colloidal materials or mixtures thereof, e.g. hydrophilic natural colloids, modified hydrophilic natural colloids or synthetic hydrophilic polymers. More particularly these colloids may be selected from such film-forming natural or modified natural hydrophilic colloids as e.g. glue, casein, zein, hydroxyethyl cellulose, carboxymethyl cellulose, methyl cellulose, carboxymethyl hydroxyethyl cellulose, gum arabic, sodium alginate and hydrophilic derivatives of such colloids. They may also be selected from such synthetic hydrophilic polymers as e.g. polyvinyl alcohol, poly-N-vinyl pyrrolidone, polyvinyl amine, polyethylene oxide, polystyrene sulphonic acid, polyacrylic acid, and hydrophilic copolymers and derivatives of such polymers.

The coating compositions in accordance with our invention may be coated on a transparent support e.g. of glass, cellulose esters, polyethylene terephthalate or on a non-transparent reflecting material such as paper or an opaque cellulose ester. It is often desirable to coat first a subbing layer on the support, this practice of subbing being well known in the art.

The coating can proceed according to any known method such as roller coating, brush coating, dip-coating, spraying, extrusion coating, etc.

The following examples illustrate the present invention.

EXAMPLE 1

A series of solutions of surface-active compounds in aqueous gelatin were prepared by adding to 50 g of dry gelatin, 30 ml of a 7% solution of Acid Violet Fuchsine Extra FB (C.I. 42685) in water and ethanol and 10 ml of a 5% solution of the surface-active compound to be tested and diluting with water to make 1 liter.

The solutions obtained were coated on a subbed cellulose triacetate support. The surface-active compounds and the results obtained therewith are given in the table hereinafter. The uniformity of the coating obtained was evaluated with the visually observed absorption of the dye in the coated layers. The number of comets given in the table is the average of comets found in 6 strips of 0.5 sq.m. each.

TABLE 2

| Surface-active agent | Structure | Nr. of comets | Uniformity of coating |
|---|---|---|---|
| saponin | natural product | 12 | good |
| HOSTAPON T (1) | $H_3C(CH_2)_7-CH=CH-(CH_2)_7-\overset{O}{\underset{\|}{C}}-\overset{CH_3}{\underset{\|}{N}}$<br>$\quad\quad\quad\quad\quad\quad\quad\quad\quad NaO_3SCH_2CH_2$ | 18 | good |
| FC.126 (2) | ammonium salt of perfluoro-caprylic acid | 1-2 | good |
| MONFLOR 31 (3) | $F_3C-F_2C\quad CF_3$<br>$\quad\quad\|\quad\quad\|$<br>$F_3C-C-C=C-O-\langle\;\rangle-SO_3Na$<br>$\quad\quad\|\quad\quad\|$<br>$F_3C-F_2C\quad CF_3$ | 16 | good |
| compound 3 | see table 1 | 1-2 | good |
| compound 4 | see table 1 | 1-2 | good |
| compound 11 | see table 1 | 4-5 | very good |
| compound 10 | see table 1 | 2 | good |
| compound 1 | see table 1 | 3 | good |
| compound 14 | see table 1 | 2 | good |

(1) HOSTAPON T is a trade name for a product having the structural formula given in the table, the product being marketed by Farbwerke Hoechst A.G., Frankfurt (am Main) - Hoechst, W-Germany.
(2) FC. 126 is a trade name for the ammonium salt of perfluorocaprylic acid marketed by Minnesota Mining and Manufacturing Company; St. Paul, Minnesota, U.S.A.
(3) MONFLOR 31 is a trade name for a 30% solution in isopropanol and water (1:2) of a product having the structural formula given in the table hereinbefore. The product is marketed by Imperial Chemical Industries Ltd., London S.W. 1, United Kingdom.

The results in the above table show that the short-chain fluorine-containing surfactants of the present invention are valuable coating aids for use in hydrophilic colloid coating compositions. They have approximately the same favourable effect of reducing the formation of comets as the FC.126-surfactant known from the Belgian patent specification No. 742,680, already mentioned hereinbefore, for use as coating aid in hydrophilic colloid coating compositions.

EXAMPLE 2

Four dispersions of TEFLON (registered trade mark of du Pont for polytetrafluoroethylene) were prepared as follows. 1 g of the compound to be tested was dissolved in 20 ml of water. 1 g of TEFLON powder was added to the solution, which was then diluted with water to make 100 ml and homogenized with an ultrasonic device. The resulting dispersion was transferred into a measuring glass.

Depending from the compound used, sedimentation of the TEFLON powder may either take place or not. The turbidity of the dispersion after a storage time of 24 hours was taken as a criterion of the efficiency of the surface-active compound.

The results obtained are given in table 2 hereinafter.

TABLE 3

| Surface-active compound | Turbidity |
|---|---|
| MERSOLAT H (1) | high |
| FC.126 (2) | low |
| compound 5 | very low |
| compound 10 | moderate to low |

(1) MERSOLAT H is a trade name for the sodium salt of an alkyl $C_{14}-C_{18}$ sulphonate marketed by Bayer A.G., Leverkusen, W-Germany.
(2) FC.126 has been identified in Example 1.

The dispersion of the TEFLON comprising the fluorinated surfactant of the present invention was incorporated in a gelatin antistress coating composition for forming a surface-coating of a photographic silver halide material.

EXAMPLE 3

An X-ray film material was used to illustrate the antistatic properties of surface-active compounds of the invention. It was prepared by coating on both sides of a subbed cellulose triacetate support a gelatin silver bromoiodide emulsion (2 mole % of iodide) containing per kg emulsion 80 g of gelatin and an amount of silver halide equivalent to 190 g of silver nitrate. The emulsion was coated on each side of the support in the ratio of 1 kg of emulsion for 27 sq.m. Both emulsion-coated sides, while still wet, were coated with a gelatin antistress layer from an aqueous gelatin composition containing per liter 30 g of gelatin, 1 g of polymethyl methacrylate particles (50% of the particles having a diameter of 5 $\mu$m) and at least one of the compounds listed in the table hereinafter. The gelatin antistress layers were coated in the ratio of approximately 27 sq.m. per liter of aqueous gelatin composition, which means that approximately 1.1 g of gelatin was present per sq.m. on each side of the support.

The resulting X-ray film material was cut into different sheets and each sheet was fed through a series of rubber rollers. During contact of the sheets with the rollers electrostatic charges could be generated and give rise to discharges or sparks.

As a rule no discharges were observed at a relative humidity of 50%. In dry conditions, however, e.g. a relative humidity of 30%, sparks are encountered, which are made visible by subsequent development of the material.

The evaluation criterion of the antistatic properties as used in table 3 hereinafter is as follows: 0 stands for excellent, 1 stands for very good, 2 stands for moderate, 3 is poor, and 4 is very poor.

TABLE 4

| Surface-active agent(s) (3 ml of a 5% aqueous solution) | Evaluation of antistatic properties (in a relative humidity of 30%) |
|---|---|
| sodium lauryl sulphate (1) | 4 |
| FC.126 (2) | 3 |
| compound 3 (3) | 3 |
| (1) + i-$C_9H_{19}$—$C_6H_4$—$(OCH_2CH_2)_{17}OH$ | 3 |
| (2) + i-$C_9H_{19}$—$C_6H_4$—$(OCH_2CH_2)_{17}OH$ | 2 |
| (3) + i-$C_9H_{19}$—$C_6H_4$—$(OCH_2CH_2)_{17}OH$ | 2 |
| (1) + $C_7F_{15}$—$CONH(CH_2CH_2O)_{17}H$ | 1–2 |
| (2) + $C_7F_{15}$—$CONH(CH_2CH_2O)_{17}H$ | 0–1 |
| (1) + compound 9 | 1–2 |
| (2) + compound 9 | 0–1 |
| (3) + compound 9 | 0–1 |

It appears clearly from this table that the short-chain fluorine-containing surfactants of the invention have at least the same antistatic activity as the known long-chain fluorine-containing surfactants.

We claim:

1. Light-sensitive silver halide material comprising a support and one or more hydrophilic colloid layers including at least one light-sensitive silver halide emulsion layer, wherein at least one hydrophilic colloid layer comprises at least one surface-active agent corresponding to the general formula:

$$(Rf—X)_n—A—L—Z$$

wherein
Rf represents a short-chain fluorine-containing group derived from hexafluoropropylene or trifluorochloroethylene, such short-chain group corresponding to one of the formulae Y—HCF—$CF_2$—, Y—CF=CF—, and $F_2C$=CF—$CF_2$— wherein Y represents chlorine or trifluoromethyl,
X represents oxygen, sulphur, or sulphonyl,
n represents an integer of at least 2, the Rf groups being same or different,
L represents a monovalent bond or a bivalent group selected from —COO—alkylene—, —CONR$^1$—alkylene—, and —$SO_2NR^1$—alkylene—, wherein R$^1$ is hydrogen or $C_1$–$C_5$ alkyl, and
Z represents a hydrophilic polyoxyethylene group or a hydrophilic group selected from the group consisting of —$SO_3M$, —$OSO_3M$, —COOM,

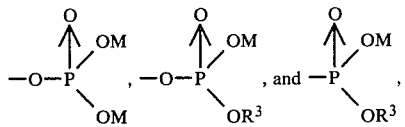

wherein M is hydrogen, an alkali metal, ammonium, or organic ammonium, and R$^3$ is alkyl, A represents a straight-chain or branched-chain aliphatic hydrocarbon group, an aromatic hydrocarbon group or a mixed aliphatic-aromatic hydrocarbon group which groups may be substituted or not; A being an aromatic hydrocarbon group when L is a monovalent bond and Z is a hydrophilic polyoxyethylene group.

2. A light-sensitive silver halide material according to claim 1, wherein said surface-active agent has been prepared by addition reaction between hexafluoropropylene or trifluorochloroethylene and hydroxy- or mercapto-substituted aliphatic or aromatic compounds containing (a) said hydrophilic group(s), or hydroxy- or mercapto-substituted aliphatic or aromatic compounds in which (a) said hydrophilic group(s) is (are) introduced subsequently.

3. A light-sensitive silver halide material according to claim 1, wherein A is phenylene, n is 2 or 3 and L—Z together are —COR wherein R is
(a) OM wherein M is hydrogen, alkali metal, ammonium, organic ammonium, or $(CH_2CH_2O)_pR^4$ wherein R$^4$ is hydrogen or $C_1$–$C_5$ alkyl, which may be substituted by carboxy, sulpho, or sulphato in acid or salt form, and p is a positive integer, or
(b)

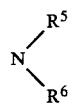

wherein R$^5$ is hydrogen or $C_1$–$C_5$ alkyl or has the same significance as R$^6$, R$^6$ is $C_1$–$C_{10}$ alkyl substituted by carboxy or sulpho in acid or salt form, or $(CH_2CH_2O)_zR^7$, wherein R$^7$ is hydrogen or $C_1$–$C_5$ alkyl, which may be substituted by carboxy, sulpho, or sulphato in acid or salt form, and z is a positive integer.

4. A light-sensitive silver material according to claim 3, wherein the said surface-active agent has been prepared by addition reaction between hexafluoropropylene or trifluorochloroethylene and a di- or trihydroxy-substituted benzoic acid, by subsequent alkaline hydrolysis, and optionally by further conversion of the carboxy group.

5. A light-sensitive silver halide material according to claim 1, wherein said surface-active agent is present in a surface coating of the light-sensitive material.

6. A light-sensitive silver halide material according to claim 5, wherein the surface coating comprises a matting agent.

7. A light-sensitive silver halide material according to claim 6, wherein the matting agent is polytetrafluoroethylene.

* * * * *